United States Patent [19]

Shults et al.

[11] 4,140,612

[45] Feb. 20, 1979

[54] GLASS ELECTRODE

[76] Inventors: Mikhail M. Shults, Prospekt Engelsa, 63, korpus 3, kv. 51; Anatoly A. Beljustin, Naberezhnaya Kanala Griboedova, 156, kv. 2; Alexandr M. Pisarevsky, Kronverskaya ulitsa, 29/37, kv. 109; Ljudmila V. Avramenko, ulitsa Timurovskaya, 6, korpus 3, kv. 76; Sergei E. Volkov, ulitsa matrosa Zheleznyaka, 29, kv.8, all of Leningrad; Vera N. Lakhtikova, ulitsa Lenina, 6, kv. 9, Chelyabinsk; Vladimir A. Dolidze, ulitsa Zakariadze, 10, kv. 10; Valentina M. Tarasova, prospekt Plekhanova, 148, kv. 19, both of Tbilisi, all of U.S.S.R.

[21] Appl. No.: 732,417

[22] Filed: Oct. 14, 1976

[51] Int. Cl.$^2$ .......................................... G01N 27/36
[52] U.S. Cl. ................................. 204/195 G; 106/52
[58] Field of Search ...................... 204/195 G; 106/52

[56] References Cited

U.S. PATENT DOCUMENTS

| | | | |
|---|---|---|---|
| 2,444,845 | 7/1948 | Perley | 204/195 G |
| 3,480,536 | 11/1969 | Arthur | 204/195 G |
| 3,558,528 | 1/1971 | Buck et al. | 204/195 G |
| 3,713,992 | 1/1973 | Akazawa | 204/195 G |
| 3,773,642 | 11/1973 | Nikolsky et al. | 204/195 G |

OTHER PUBLICATIONS

Roe, "J. of Electrochemical Soc.", vol. 112, No. 10, Oct. 1965, pp. 1005–1009.

*Primary Examiner*—T. Tung
*Attorney, Agent, or Firm*—Robert E. Burns; Emmanuel J. Lobato; Bruce L. Adams

[57] ABSTRACT

According to the present invention, a glass electrode for measuring the oxidation potential of liquid media comprises a tubular casing made of a high-resistance glass. A sensing element is tightly sealed to the tube and is rigidly connected to a current lead disposed within the tube. The sensing element is made of a glass featuring electronic conduction and containing tri- and tetravalent titanium oxides and those of pentavalent niobium and/or tantalum, at the following ratio of the components taken in parts by weight:

$SiO_2$—35 to 45
$Me_2O$—7.0 to 26, wherein Me is Li, Na, K
$TiO_2$—16 to 40
$Ti_2O_3$—0.8 to 4.2
$Nb_2O_5$ and/or $Ta_2O_5$—2.0 to 32

The use of the proposed electrode made it possible to measure the oxidation potentials ranging from −700 to 1250 mV in solutions having a pH of from −0.5 to 14, at the temperatures ranging from 0 to 150° C., in the presence of dissolved oxygen, hydrogen and catalyst poisons.

6 Claims, 1 Drawing Figure

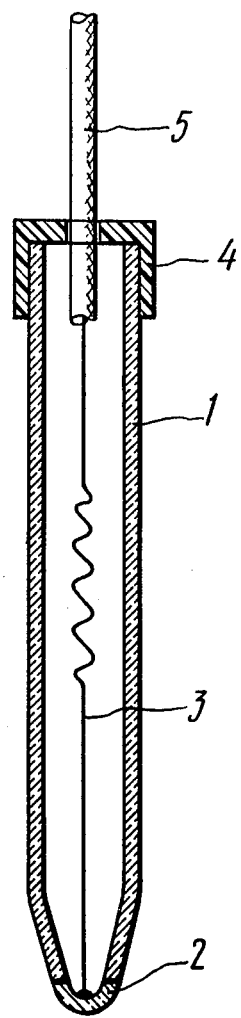

GLASS ELECTRODE

BACKGROUND OF THE INVENTION

The present invention relates to devices for the potentiometric analysis of liquid media and, more particularly, to glass electrodes designed for measuring the oxidation potentials of liquid media over a wide range.

The proposed electrodes will find suitable application in the sensing elements of the systems for the continuous control and monitoring of technological processes in the chemical, pulp- and paper-making, textile, pharmaceutical and microbiological industries as well as in hydrometallurgy.

Electrodes are known in the art for measuring the oxidative potentials in liquid media, comprising sensing elements made of noble metals, such as platinum and gold. These electrodes have the following disadvantages:

sensing elements made of noble metals are susceptible of a comparatively easy contamination by catalyst poisons (for instance, by $SO_2$ and other sulphurous compounds);

the presence of gaseous oxygen or hydrogen in a medium being analyzed affects the electrode potential;

noble metals are capable of catalyzing the decomposition of some redox systems (for instance, of hydrogen peroxide).

A glass electrode is also known for measuring the oxidative potential of liquid media, comprising a tubular casing made of a high-resistance glass, having one end thereof tightly sealed to a sensing element being rigidly connected to a current lead disposed within the tube.

The sensing element is made of a glass featuring electronic conduction and consisting of 45 to 65 wt.% $SiO_2$, 25-50 wt.% $Fe_2O_3$, 4 to 15 wt.% $Na_2O$, 2 to 10 wt.% $Li_2O$.

A significant disadvantage inherent in these electrodes resides in their inability to serve as indicators of the oxidation potentials in strongly acid media having a pH value of below 3, at a temperature of above 60° C.

SUMMARY OF THE INVENTION

It is an object of the present invention to provide an ever greater scope of application of glass electrodes for heavily acid media at a temperature above 60° C in the presence of dissolved oxygen, hydrogen and catalyst poisons.

It is an object of the present invention to provide such glass electrode, wherein the sensing element is made of a material which enables the glass electrode to measure the oxidation potential of liquid media having a pH value of below 3 at a temperature of above 60° C., in the presence of dissolved oxygen, hydrogen and catalyst poisons.

This object is attained by a glass electrode for measuring the oxidation potential of liquid media, comprising a tubular casing made of a high-resistance glass, having one end thereof tightly sealed to a sensing element which is rigidly connected to a current lead disposed within said tube which is made of a glass featuring electronic conduction and containing silica and alkali metal oxides; according to the present invention, the sensing element is made of a glass featuring electronic conduction and containing oxides of tri- and tetravalent titanium and those of pentavalent niobium and/or tantalum, at the following ratio of the components taken in parts by weight:

$SiO_2$—32 to 45
$Me_2O$—7.0 to 26.0, wherein Me is Li, Na, K
$TiO_2$—16.0 to 40
$Ti_2O_3$—0.8 to 4.2
$Nb_2O_5$ and/or $Ta_2O_5$—2.0 to 32.0

DESCRIPTION OF THE INVENTION

The fact that the sensing element of the glass electrode of the invention is made of a glass featuring electronic conduction and containing oxides of tri- and tetravalent titanium, provides for considerable increase in the chemical stability of said glass and enables the oxidation potentials to be measured in liquid media having a pH value of below 3.

Due to introducing relatively large amounts of titanium oxides into glass and due to a pre-determined ratio between their two different valent forms, and namely:

$$\frac{Ti(III)}{Ti(III) + Ti(IV)} = 0.08 \text{ to } 0.20$$

a required level of electronic conduction is attained in the glass constituting the sensing element.

On introducing titanium oxides in an amount of below 16 parts by weight into said glass, its resistivity exceeds $10^8$ ohm.cm whereby its use for redox measurements is rendered impossible by reason of a small value of exchange currents at the glass-solution interface.

Excessive concentrations of titanium oxides (above 40 parts by weight) result in complete crystallization of the aforementioned glass in the process of its manufacture, rendering it unfit for the electrode sensing element to be made thereof.

From the foregoing, however, it will be apparent that it is possible to improve the stability of the electrode readings and to prolong the service life of this type of electrode when in operation in liquid media having a pH value of below 3.

The presence of oxides of $Nb_2O_5$ and/or $Ta_2O_5$ in the composition of a glass employed for the manufacture of the sensing element of the proposed electrode renders the glass structure more compact, whereby its chemical stability is increased.

Introducing $Nb_2O_5$ into the glass composition in an amount of below 2 parts by weight exerts no positive effect on the properties of said glass, while increasing the amount of $Nb_2O_5$ above 32 parts by weight results in crystallization thereof.

The mechanism of the action of $Ta_2O_5$ in said glass is similar to that of $Nb_2O_5$; too high $Ta_2O_5$ concentrations result in a loss in the mechanical strength of the glass used for the manufacture of the sensing element.

The introduction of oxides of pentavalent niobium and tantalum into the composition of said glass enables the glass electrode to extend the range of potentiometric measurements towards the region of high positive values of the oxidative potentials (up to 1.5 V in relation to a conventional hydrogen electrode), in strongly acid media, at temperatures in excess of 60° C., in the presence of dissolved oxygen, hydrogen and catalyst poisons.

It is expedient that the sensing element of the glass electrode be made of a glass featuring electronic conduction and containing the following components taken in parts by weight:

$SiO_2$—32 to 37.4

$Li_2O$—0 to 1.8
$Na_2O$—5.0 to 8.3
$K_2O$—2.2 to 10.7
$TiO_2$—26 to 40
$Ti_2O_3$—0.8 to 1.7
$Nb_2O_5$—4.0 to 25.0

The use of such a sensing element in the glass electrode simplifies to a significant extent the electrode production process.

It is preferable that the sensing element of the glass electrode be made of a glass featuring electronic conduction, at the following ratio of the components taken in parts by weight:
$SiO_2$—37.1 to 45
$Na_2O$—5.0 to 8.0
$K_2O$—6.3 to 17.4
$Li_2O$—1.8 to 3.1
$TiO_2$—16 to 31.8
$Ti_2O_3$—1.7 to 4.2
$Nb_2O_5$—10.7 to 21.2
$Ta_2O_5$—2 to 21.3

High concentrations of trivalent titanium in said glass make it possible to manufacture sensing elements by casting molten glass in to a mould. The sensing elements thus produces are characterized with a pre-determined Ti(III)-to-Ti(IV) ratio and offer reproducible values of their electrical parameters.

The herein proposed electrode makes it possible to measure the oxidation potentials over a range extending from −700 to 1250 mV in relation to the conventional hydrogen electrode, in solutions having pH values ranging from −0.5 to 14, at a temperature between 0° C. and 150° C. in the presence of dissolved oxygen, hydrogen and catalyst poisons.

The proposed invention will be better understood from the following description of a specific embodiment thereof, with reference to the accompanying drawing, wherein:

FIG. 1 is a longitudinal sectional view of the proposed glass electrode for measuring the oxidation potential of liquid media, according to the invention.

The glass electrode (FIG. 1) for measuring the oxidative potentials of liquid media is made in the form of a cylindrical tube 1 of a high-resistance glass, which tube serves as a casing. A sensing element 2, secured by soldering to one end of the tube 1, is made of a glass featuring electronic conduction, composed, according to the invention, of 32 to 45 parts by weight $SiO_2$, 7.0 to 26.0 parts by weight $Me_2O$, wherein Me is Li, Na, K, 16.0 to 40 parts by weight $TiO_2$, 0.8 to 4.2 parts by weight $Ti_2O_3$, 2.0 to 32.0 parts by weight $Nb_2O_5$ and/or $Ta_2O_5$. The sensing element 2 is connected to a metallic current lead 3 disposed with the cylindrical tube 1 and led out of it in the form of a cable 5 through the top of said tube protected by a cap 4 which ensures hermeticity of the inner cavity of the electrode.

The glass electrode and an auxiliary electrode, for instance, a chloro-silver electrode, are immersed in a solution containing a redox system. Potentials arise in a circuit thus formed, and in the event of the glass electrode, these arise at the sensing element glass-solution interphase. The potential of the glass electrode depends on the redox state of a medium, whereas that of the accessory electrode remains always constant. The current leads of these electrodes are connected to a measuring instrument, a high-resistance millivoltmeter which registers the arising potential difference determining the ratio at which the oxidized and reduced forms of elements occur in the solution being analyzed according to the Nernst equation.

The proposed electrode makes it possible to measure the oxidative potentials within the range of from −700 to 1250 mV at pH values ranging from −0.5 to 14. The electrode can operate within a temperature range of from 0 to +150° C., at an electrical resistance of $\leq 10$ Mohm.

Given herein below are examples for the specific compositions of glasses which can be used for the manufacture of the proposed electrode.

The compositions of these glasses were selected on the basis of study of the electrical and electrode properties of solutions of redox systems, of determining indifference boundaries by the charging curves method, as well as on the basis of study of processing characteristics.

Two types of the production processes of the proposed electrodes have been developed depending on different valent forms of titanium in the glass compositions.

First production process.

Titanium is introduced into a charge both in the form of $TiO_2$ and $Ti_2O_3$. A quartz crucible containing the charge is placed into a furnace pre-heated up to a temperature of 1200° C.; the temperature is further increased up to 1400–1550° C., and the crucible with the charge is maintained at this temperature for some 2.5 to 5 hours. Glass melting is carried out at a continuous blowing of an inert gas. On completion of the melting stage of the process, molten glass is poured into a mold to form glass rods. The electrodes are manufactured by melting glass in the flame of a gas-oxygen burner. The glass melt is transferred to the open end of a cylindrical glass tube 1, heated up and blown out to form a semisphere. Prior to introducing a current lead 3 into the inner cavity of the cylindrical tube 1, a thin layer of glass is removed from the outer and inner surfaces of the resultant semisphere, since the composition and structure of had underwent inserted in the process of connecting a sensing element to the electrode casing in the flame of a gas-oxygen burner.

Second production process.

Glass is synthesized according to the first production process at a temperature of 1450 to 1600° C., in the atmosphere of inert gas. Molten glass is further cast into special molds wherein filaments made of refractory metals had been inserted in advance to serve as current leads for the forming electrodes. The resultant sensing elements are transferred to a muffle furnace heated up to a temperature of 450 to 500° C. wherein they are annealed for 10 hours. The sensing elements are then tightened in tubes made of a material of high insulating properties. The glass compositions are set forth in Table 1.

In the hereinbelow cited solutions of redox systems, the proposed electrodes exhibit definite values of oxidation potentials.

EXAMPLE 1

A glass electrode is immersed into some 200 ml of a buffer solution having a pH value of 6.86 and containing 5.795 g $K_3(FeCN)_6$ and 1.208 g $K_4(FeCN)_6 \cdot 3H_2O$. The sensing element of this glass electrode can be manufactured of any glass whose composition is set forth in Table 1. The oxidation potential of the glass electrode measured in said solution in relation to a chloro-silver electrode was found to be equal to +294 ± 10 mV at a temperature of 25° C.

EXAMPLE 2

A glass electrode is immersed into some 200 ml of an 1 N-solution of sulphuric acid wherein 0.511 g Fe$_2$(SO$_4$)$_3$. 9H$_2$O and 6.63 g FeSO$_4$.7H$_2$O are dissolved. The sensing element of this glass electrode can be manufactured of any glass whose composition is set forth in Table 1. The oxidation potential of the glass electrode measured in said solution in relation to a saturated chloro-silver electrode is equal to +405 ± 10 mV at a temperature of 25° C.

EXAMPLE 3

A glass electrode is immersed into some 200 ml of an 1 N-solution of sulphuric acid wherein 4.213 g Fe$_2$(SO$_4$)$_3$.9H$_2$O and 1.38 g FeSO$_4$.7H$_2$O are dissolved. The sensing element of this glass electrode can be manufactured of any glass whose composition is set forth in Table 1. The oxidation potential of the glass electrode measured in said solution in relation to a saturated chloro-silver electrode was equal to +496 ± 10 mV at a temperature of 25° C.

EXAMPLE 4

Use is made in this Example of a buffer solution prepared with 27.2 g CH$_3$COOH and 170 ml HCl dissolved in 1 liter of water. A glass electrode is immersed into some 200 ml of said buffer solution wherein 4.28 g KIO$_3$ and 10 ml of a 10%-solution of I$_2$ in alcohol are dissolved. The sensing element of this glass electrode can be manufactured of any glass whose composition is set forth reported in Table 1. The oxidation potential of the glass electrode measured in said solution in relation to a saturated chloro-silver electrode was equal to 720 ± 10 mV at a temperature of 25° C.

EXAMPLE 5 chlorosilver

A glass electrode is immersed into 1 liter of a 0.5 N-solution of sulphuric acid wherein 3.56 g Ce(SO$_4$)$_2$.4H$_2$O and 4.34 g Ce(NO$_3$)$_3$.6H$_2$O are dissolved. Any of the glasses whose compositions are set forth in Table 1 can be used for the manufacture of the sensing element of said glass electrode. The oxidation potential of the glass electrode measured in said solution in relation to a saturated chloro-silver electrode was equal to +1235 ±10 mV at a temperature of 25° C.

EXAMPLE 6

A glass electrode is immersed into some 250 ml of a 0.1 N-solution of hydrochloric acid wherein 0.97 g Fe$_2$O$_3$.H$_2$O are dissolved. Any of the glasses whose compositions are set forth in Table 1 can be used for the manufacture of the sensing element of this glass electrode. There follows an electrolysis at a current intensity of 8·10$^{-3}$ A for 1 hour in a protective atmosphere provided by an inert gas. The oxidation potential of the glass electrode measured in said solution in relation to a saturated chloro-silver electrode was equal to −700 ± 10 mV at a temperature of 25° C.

Table 1

| Oxides | Glass 1 parts by weight | Glass 2 parts by weight | Glass 3 parts by weight | Glass 4 parts by weight | Glass 5 parts by weight | Glass 6 parts by weight | Glass 7 parts by weight | Glass 8 parts by weight |
| --- | --- | --- | --- | --- | --- | --- | --- | --- |
| Na$_2$O | 5.3 | 5.4 | 8.3 | 5.0 | 6.5 | 8.6 | 8.3 | 7.7 |
| K$_2$O | 2.2 | 6.4 | 10.7 | 3.2 | — | 17.4 | 6.3 | 5.8 |
| Li$_2$O | — | — | — | 1.8 | 3.1 | — | — | — |
| TiO$_2$ | 26.5 | 23.4 | 40.0 | 16.0 | 21.1 | 31.8 | 27.0 | 24.7 |
| Ti$_2$O$_3$ | 3.4 | 0.8 | 4.2 | 4.1 | 3.8 | 2.9 | 3.2 | 4.2 |
| Nb$_2$O$_5$ | 25.2 | 11.4 | 4.0 | 21.2 | 8.7 | 5.3 | 10.7 | 19.4 |
| Ta$_2$O$_5$ | — | 20.6 | — | 10.3 | 11.8 | — | — | — |
| SiO$_2$ | 37.4 | 32.0 | 32.8 | 38.4 | 45 | 34 | 44.5 | 38.1 |

What is claimed is:

1. A glass electrode for measuring oxidation potentials of fluid media, comprising:
   a tubular casing made of a high-resistance glass;
   a sensing element tightly sealed to an end of said tubular casing;
   a current lead disposed within said tubular casing and rigidly connected to said sensing element,
   said sensing element being made of a glass featuring electronic conduction and consisting of
   32 to 45 parts by weight SiO$_2$;
   7.0 to 26 parts by weight Me$_2$O, wherein Me is selected from at least two alkali metals of the group consisting of Li, Na and K;
   16.0 –40 parts by weight TiO$_2$;
   0.8 –4.2 parts by weight Ti$_2$O$_3$; and
   2.0 –32 parts by weight M$_2$O$_5$, wherein M is a metal selected from the group consisting of Nb, Ta and a mixture thereof.

2. A glass electrode as claimed in claim 1, wherein said sensing element is made of a glass featuring electronic conduction and consisting of
   32.0–37.4 parts by weight SiO$_2$;
   0–1.8 parts by weight Li$_2$O;
   5.0–8.3 parts by weight Na$_2$O;
   2.2–10.7 parts by weight K$_2$O;
   26.0–40 parts by weight TiO$_2$; 0.8–1.7 parts by weight Ti$_2$O$_3$ and
   4.0–25 parts by weight Nb$_2$O$_5$.

3. A glass electrode as claimed in claim 1, comprising said sensing element made of glass featuring electronic conduction and consisting of 37.1–45 parts by weight SiO$_2$, 5.0–8.0 parts by weight Na$_2$O, 6.3–17.4 parts by weight K$_2$O, 1.8–3.1 parts by weight Li$_2$O, 16–31.8 parts by weight TiO$_2$, 1.7–4.2 parts by weight Ti$_2$O$_3$, 10.7–21.2 parts by weight Nb$_2$O$_5$ and 2.0–21.3 parts by weight Ta$_2$O$_5$.

4. A glass electrode as claimed in claim 1, wherein said glass contains Na$_2$O in combination with at least one additional alkali metal oxide selected from the group consisting of Li$_2$O and K$_2$O.

5. A glass electrode as claimed in claim 4, in which said glass contains about 5.0 to 8.6 parts by weight of Na$_2$O, about 0 to 17 parts by weight of K$_2$O and about 0 to 3.1 parts by weight of Li$_2$O.

6. A glass electrode as claimed in claim 1, in which said glass contains about 4.0 to 25.2 parts by weight of Nb$_2$O$_5$ and about 0 to 20.6 parts by weight of Ta$_2$O$_5$.

* * * * *